United States Patent [19]

Oxenrider et al.

[11] Patent Number: 4,939,289

[45] Date of Patent: Jul. 3, 1990

[54] FIBER SURFACE MODIFIERS

[75] Inventors: Bryce C. Oxenrider, Morris, N.J.; David J. Long, Amherst, N.Y.

[73] Assignee: Allied-Signal Inc., Morris Township, Morris County, N.J.

[21] Appl. No.: 190,987

[22] Filed: May 6, 1988

Related U.S. Application Data

[63] Continuation-in-part of Ser. No. 765,629, Aug. 15, 1985, abandoned.

[51] Int. Cl.$^5$ .................... C07C 69/76; C07C 327/25; C07D 303/08; C07F 7/04
[52] U.S. Cl. .................................. 560/87; 427/412.5; 428/473.5; 428/475.2; 549/551; 556/418; 558/251; 560/76
[58] Field of Search ......................... 560/87; 556/418; 549/551; 558/251

[56] References Cited

U.S. PATENT DOCUMENTS

| | | | |
|---|---|---|---|
| 4,435,294 | 3/1984 | Oxenrider et al. | 252/8.6 |
| 4,446,306 | 5/1984 | Oxenrider | 560/87 X |
| 4,460,785 | 7/1984 | Oxenrider et al. | 560/83 |
| 4,551,519 | 11/1985 | Oxenrider | 560/87 X |
| 4,604,316 | 8/1986 | Thomas et al. | 560/87 X |

FOREIGN PATENT DOCUMENTS

| | | |
|---|---|---|
| 1102344 | 6/1981 | Canada . |
| 1543081 | 3/1979 | United Kingdom . |

*Primary Examiner*—Werren B. Lone
*Assistant Examiner*—Vera C. Clarke
*Attorney, Agent, or Firm*—Richard C. Stewart, II; Gerhard H. Fuchs

[57] ABSTRACT

This invention relates to fiber surface treating agents containing a pyromellitate nucleus which have fungicidal, anti-microbial and anti-static properties, and blends of such agents with other types of surface modifiers.

15 Claims, No Drawings

FIBER SURFACE MODIFIERS

RELATED APPLICATION

This application is a continuation-in-part application of U.S. patent application Ser. No. 765,629, filed Aug. 15, 1985, now abandoned.

BACKGROUND OF THE INVENTION

1. Field of the Invention

This invention relates to fiber surface treating agents. More particularly, this invention relates to such agents containing a pyromellitate nucleus which have fungicidal, anti-microbial and anti-static properties, and blends of such agents with other types of surface modifiers.

2. Prior Art

U.S. Pat. No. 4,209,610 discloses that benzene diacid-diesters may be synthesized by reacting fluorinated alcohols with pyromellitic dianhydride. Upon treatment with epoxide-containing organic radicals, the diacid-diesters react to form partially fluorinated esters of benzene carboxylic acids. The partially fluorinated esters are used as water and soil repellents in various fibers. This patent also discloses that trimesic acid may be converted to trimesoyl trichloride which yields partially fluorinated esters that are useful as soil and water repellants in various fibers.

United Kingdom Pat. No. 1,543,081 discloses that fluorinated ester-acids may be synthesized by reacting phthalic anhydride with fluorinated alcohols. The above-referenced British patent further discldses that the resulting ester-acids may be converted to ester-acid chlorides, which in a subsequent step may be reacted with various reagents to form soil and water repelling agents.

Canadian Pat. No. 1,102,344 describes numerous fluorocarbon compounds which are useful as soil and water repelling agents for various fibers. Included amongst these compounds are fluorocarbon esters of phthalic anhydride wherein the ester-acid chloride of phthalic anhydride is used as an intermediate in the synthesis of the fluorocarbon oil and water repelling agent.

SUMMARY OF THE INVENTION

This invention relates to novel compounds which have fungicidal, antimicrobial and anti-static properties when applied to the surface of various fibers. More particularly, the compounds of this invention are of the formula:

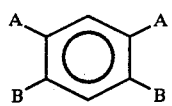 (I)

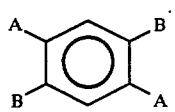 (II)

or oligomers thereof wherein two or more compounds (I) and/or (II) are linked at the "B" substitution sites by divalent moieties of the formula:

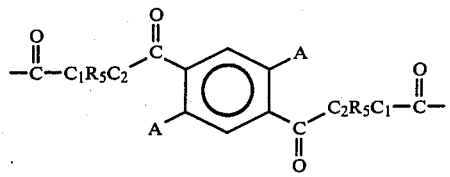

or

or

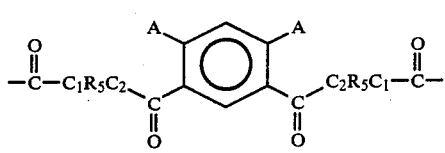

wherein:

B is a moiety of the formula:

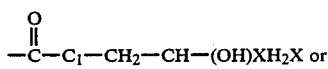

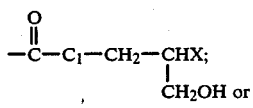

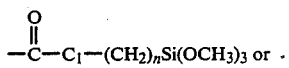

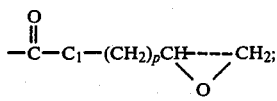

A is a moiety of the formula:

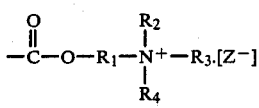

$R_1$ is divalent alkylene having from 1 to about 4 carbon atoms;

$R_2$ and $R_3$ are the same or different and are alkyl having from 1 to about 3 carbon atoms;

$R_4$ is alkyl having from about 1 to about 20 carbon atoms,

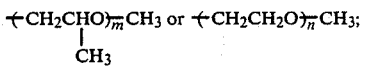

n is an integer from 1 to about 10;

Z is chloride, bromide or iodide;

m is an integer from 1 to about 10;

p is 0 to about 4;

$C_1$ and $C_2$ are the same or different and are divalent oxygen, sulfur, amino or alkylamino; and $R_5$ is substituted or unsubstituted alkylene having from 1 to about 10 carbon atoms or arylene wherein permissible substituents are one or more halo or hydroxy groups.

Fibers modified with these compounds are laundry stable, and have lower surface resistivity. Certain of these compounds also impart fungicidal and antimicrobial activity.

DESCRIPTION OF THE PREFERRED EMBODIMENTS

The compounds of this invention are of the formula:

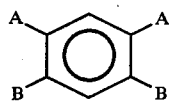  (I)

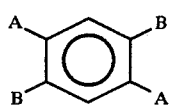  (II)

or oligomers thereof wherein A and B are as described above. Illustrative of suitable "B" groups in the monomeric embodiments of this invention and as non-linking "B" groups in the oligomeric embodiments of the invention are moieties of the formula:

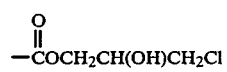   

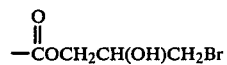   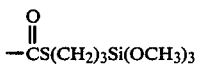

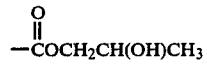   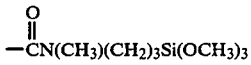

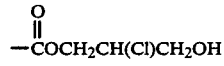   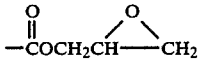

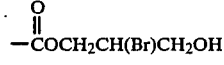   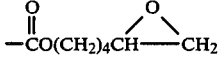

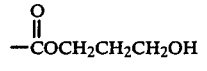   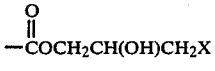

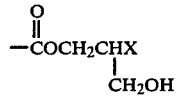   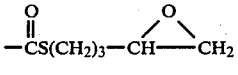

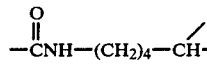   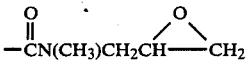

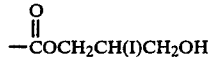   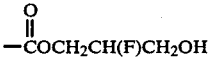

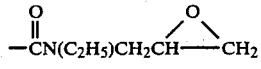   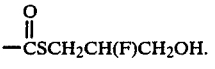

Illustrative "B" linking groups in oligomeric compounds of this invention are:

-continued

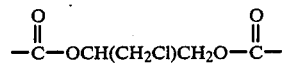

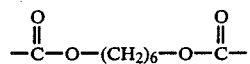

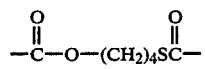

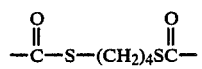

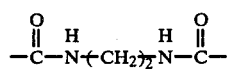

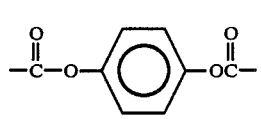

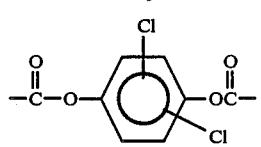

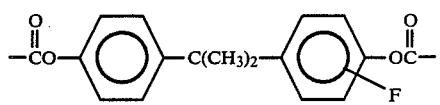

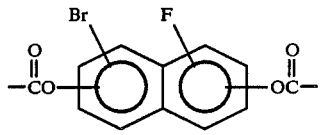

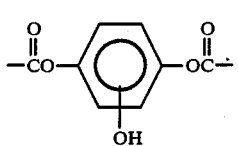

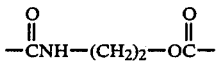

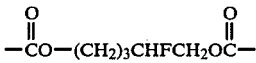

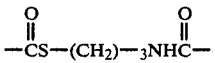

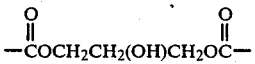

-continued $$-\overset{O}{\underset{\|}{C}}S(CH_2)_2-CHB-(CH_2)_2-O\overset{O}{\underset{\|}{C}}-$$

$$-\overset{O}{\underset{\|}{C}}OCH_2CH(Cl)CH_2O\overset{O}{\underset{\|}{C}}-$$

$$-\overset{O}{\underset{\|}{C}}-O-\text{C}_6H_4-CH_2-\text{C}_6H_3(OH)-O\overset{O}{\underset{\|}{C}}-$$

$$-\overset{O}{\underset{\|}{C}}-O-\text{C}_6H_4-\text{C}_6H_3(F)-O\overset{O}{\underset{\|}{C}}-$$

$$-\overset{O}{\underset{\|}{C}}-O-\text{C}_6H_3(HO)-\text{(Cl)}-O\overset{O}{\underset{\|}{C}}-$$

$$-\overset{O}{\underset{\|}{C}}-O-CH_2-C(Cl)_2-CH_2-O\overset{O}{\underset{\|}{C}}-$$

$$-\overset{O}{\underset{\|}{C}}-O-\text{naphthyl}-CH_2CF_2CH_2-O\overset{O}{\underset{\|}{C}}$$

$$-\overset{O}{\underset{\|}{C}}-NH-\text{anthracenyl}-O\overset{O}{\underset{\|}{C}}-$$

$$-\overset{O}{\underset{\|}{C}}-NH-\text{naphthyl}-NH\overset{O}{\underset{\|}{C}}-$$

Suitable "A" groups include moieties of the formula:

$$-\overset{O}{\underset{\|}{C}}O(CH_2)_3-\overset{+}{\underset{\underset{CH_3}{|}}{N}}(CH_3)-(CH_2CH_2)_n-CH_3.[Z^-]$$

wherein n is 0 to about 9, and X is chloride, bromide or iodide. Illustrative of other "A" groups are moieties of the formula:

$$-\overset{O}{\underset{\|}{C}}O-(CH_2)_3-\overset{+}{\underset{\underset{CH_3}{|}}{N}}(CH_3)(CH_2CH_2O)_{\overline{m}}CH_3.[Z^-] \text{ or}$$

$$-\overset{O}{\underset{\|}{C}}O-(CH_2)_3-N-[CH_2CH(CH_3)]_m-O\,)CH_3.[Z^-]$$
$$\underset{CH_3}{\underset{|}{\overset{+}{|}}}$$

wherein m is 1 to about 6, and X⁻ is chloride, bromide or iodide.

Preferred compounds are those in which "B" is a moiety of the formula:

$$-\overset{O}{\underset{\|}{C}}OCH_2CH(OH)CH_2Cl \text{ or } -\overset{O}{\underset{\|}{C}}OCH_2CH(OH)CH_2Br$$

$$-\overset{O}{\underset{\|}{C}}O(CH_2)_3Si(OCH_3)_3 \text{ or } -\overset{O}{\underset{\|}{C}}OCH_2CH\overset{\overset{O}{\diagup\diagdown}}{\phantom{X}}CH_2$$

and, A is a moiety of the formula;

$$-\overset{O}{\underset{\|}{C}}O-(CH_2)_3-\overset{+}{\underset{\underset{CH_3}{|}}{N}}(CH_3)-(CH_2CH_2)_nCH_2CH_3.[Z^-]$$

where n is 0 to about 8, and Z⁻ is chloride, bromide or iodide; or $$-\overset{O}{\underset{\|}{C}}O-(CH_2)_3-\overset{+}{\underset{\underset{CH_3}{|}}{N}}(CH_3)-(CH_2CH_2O)_{\overline{m}}CH_3.[Z^-]$$

where m is from about 2 to about 10, and Z⁻ is chloride, bromide or iodide; or $$-\overset{O}{\underset{\|}{C}}O-(CH_2)_3-\overset{+}{\underset{\underset{CH_3}{|}}{N}}(CH_3)+CH_2CH(CH_3)O\,)_{\overline{o}}CH_3.[Z^-]$$

wherein o is from 1 to about 6, and Z⁻ is chloride, bromide or iodide.

Particularly preferred compounds are those in which: B is a moiety of the formula:

$$-\overset{O}{\underset{\|}{C}}OCH_2CH(OH)CH_2Cl$$

and, A is a moiety of the formula:

$$-\overset{O}{\underset{\|}{C}}O-(CH_2)_3-N-\overset{+}{\underset{\underset{CH_3}{|}}{(CH_2CH_2)_{\overline{n}}}}CH_3.[Z^-]$$

where n is from 0 to about 8, and Z⁻ is chloride or bromide; or $$-\overset{O}{\underset{\|}{C}}O-(CH_2)_3-N-\overset{+}{\underset{\underset{CH_3}{|}}{(CH_2CH_2O)_{\overline{m}}}}CH_3.[Z^-]$$

where m is from about 2 to about 4, and Z⁻ is chloride or bromide.

The monomeric compounds of this invention in which "A" is not a linking group can be conveniently prepared in two steps in accordance with the procedures described in detail in U.S. Pat. Nos. 4,209,610, 4,440,308, 4,252,982; and 4,321,403. In the procedure, pyromellitic dianhydride (PMDA) is reacted with 2 moles of quaternary ammonium alcohol, and the resulting diester diacid adduct is then reacted with an appropriate "B" precursor group in accordance with the following reaction scheme:

Reaction Scheme I

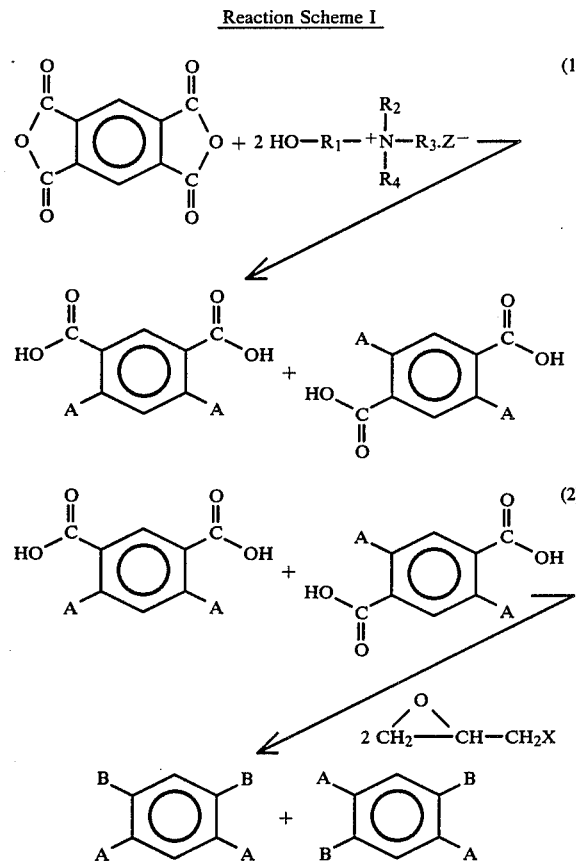

Alternately, monomeric compounds of this invention in which "A" is not a linking group can be prepared through use of the procedure described in U.S. Pat. No. 4,460,785. In this procedure, the pyromelitic dianhydride is reacted with 2 moles of the quaternary ammonium alcohol to form the corresponding diacid/diester adduct, which is then reacted with a chlorinating agent such as thionyl chloride, or oxalyl chloride or phosphorous trichloride to form the diester/diacid chloride. The chloride is then reacted with the desired mercapto, amino, halo/hydroxy or hydroxy compound to form the desired compound of this invention as depicted in Reaction Scheme II:

Reaction Scheme II

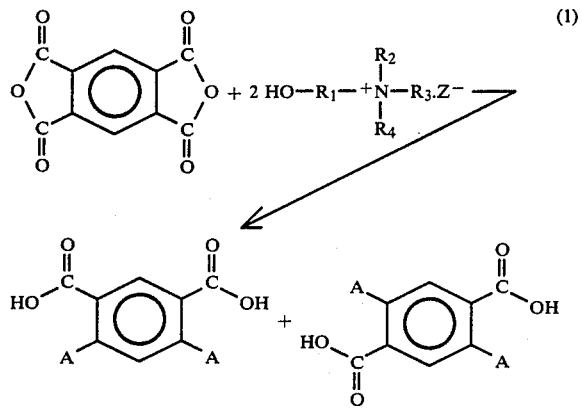

-continued
Reaction Scheme II

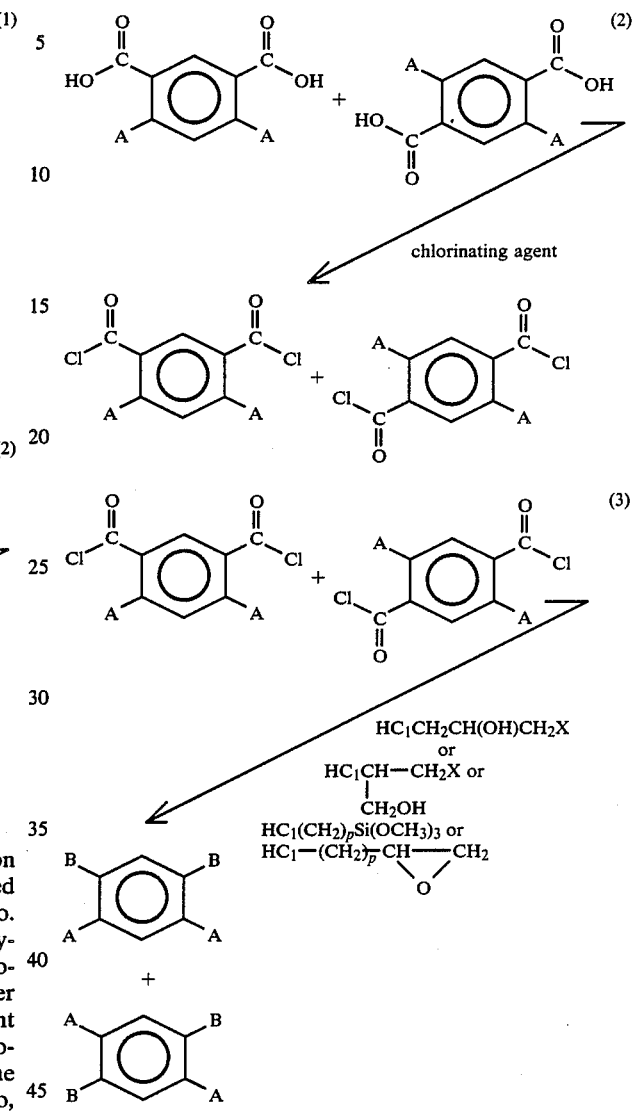

In the above Reaction Schemes I and II, $R_1$, $R_2$, $R_3$, $R_4$ A, B, $C_1$, p, Z, n, and X are as discussed above. $C_1$ is preferably oxygen.

In Reaction Schemes I and II, the first reactant is pyromellitic dianhydride (PMDA) which is normally greater than 98% purity. Common impurities which can be tolerated in minor amounts include pyromellitic monoanhydride. PMDA is well known to those of skill in the art and can be readily prepared in accordance with known procedures or can be obtained from commercial source.

In Reaction Schemes I and II, the second reactant is a quaternary ammonium alcohol of the formula:

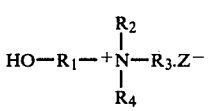

wherein $R_1$, $R_2$, $R_3$, $R_4$ and $Z^-$ are as described above. While any such alcohol having at least one relatively long aliphatic group bonded to the nitrogen can be used, preferred alcohols are those in which:

$R_1$ is alkylene having from 1 to about 3 carbon atoms;
$R_2$ and $R_3$ are individually ethyl or methyl;
$R_4$ is a moiety of the formula $(-CH_2CH_2-)_nCH_2CH_3$, $(-CH_2CH_2O-)_mCH_3$ or $(-CH_2CH(CH_3)O-)_oCH_3$, where n is 0 to about 8, m is about 2 to about 4 and o is 1 to about 6; and
$Z^-$ is chloride, bromide or iodide.

Amongst the preferred alcohols, particularly preferred alcohols are those in which $R_2$ and $R_3$ are methyl.

The third reactant used in Reaction Scheme I above is a compound which when substituted with the carboxylic acid moiety will provide the desired "B" moiety. This reactant is preferably epichlorohydrin. In the preferred embodiment of the invention, the reactant may also be the corresponding bromo compound known as epibromohydrin or may be glycidol or propylene oxide. In these preferred embodiments, it will be appreciated that all three of these compounds are three carbon oxiranes with the third carbon being of the formula $-CH_2X$ wherein X is chlorine, bromine, hydrogen or hydroxy.

The fourth reactant used in step 3 of Reaction Scheme II is a chlorinating agent such as oxalyl chloride, phosphorous trichloride, phosgene/DMF, thionyl chloride and the like. The preferred chlorinating agent is oxalyl chloride.

The fifth reactant used in step 4 of Reaction Scheme II is a substituted hydroxy, amino or mercapto compound necessary to provide the desired "B" moiety when reacted with the acyl moiety. In the preferred embodiments of the invention, this reactant is a compound wherein $C_1$ is hydroxy and X is chloro or bromo and n and p are 1.

The order of reaction for the processes of Reaction Schemes I and II is to first react the quaternary ammonium alcohol with PMDA to form the corresponding symmetrical and unsymmetrical diester/diacids. In Reaction Scheme I, the symmetrical and unsymmetrical diester/diacids are reacted with the oxirane compound to form the desired compounds I and II. In Reaction Scheme II, the diester/diacid is reacted with the chlorinating agent to provide the corresponding diester/diacid chlorides which are then reacted with the desired hydroxy, mercapto or amino compound to provide the desired compounds (I) and (II).

The mole ratios of reactants in the first step of the process is critical to whether the monomeric products or the oligomeric product is formed. If the mole ratio of reactants in the first reaction step of reaction Schemes I and II is two moles of quaternary ammonium alcohol for each mole of PMDA, the symmetrical and assymetrical diester/diacids are produced. Further reaction of these diester/diacids with a compound for forming the "B" moiety such as epichlorohydrin or epibromohydrin (which is preferably added after the first step is complete) in Reaction Scheme I, or chlorination of these diester/diacids followed by reaction with an appropriate alcohol, mercapto or amino compound in Reaction Scheme II would then produce the monomeric products (I) and (II).

The oligomeric compounds of this invention can be prepared by modification of the procedure of U.S. Pat. No. 4,446,306. For example, oligomeric compounds of this invention in which "B" linking groups are derived from oxirane compounds can be conveniently prepared using a modification of Reaction Scheme I. In Reaction Scheme I, if less then two moles of quaternary ammonium alcohol is used, the intermediate reaction mixture contains quaternary ammonium esters, free acid and unreacted anhydride groups. Taking the simplest case of one mole of quaternary ammonium alcohol for each mole of PMDA, the product will, on average, have only one quaternary ammonium ester group on a pyromellitate, the adjacent position on the pyromellitate being free acid and the two other positions (the 4-carbon and the 5-carbon of the ring) still linked by anhydride. It will be appreciated, however, that this product represents only an average, with the actual reaction mixture containing some unreacted PMDA, some of this acid/ester/anhydride and some diester/diacid. In the absence of steric factors or other considerations affecting reaction rate, one would expect a distribution of these three products of 1:2:1 when one mole of quaternary ammonium alcohol is used for each mole of PMDA. The use of more than one mole of quaternary ammonium alcohol per mole of PMDA would be expected to increase the amount of diacid/diester in the product, while the use of less than one mole of quaternary ammonium alcohol per mole of PMDA would be expected to decrease the amount of diester/diacid in the product with a resultant increase of unreacted PMDA. This mixed intermediate reaction mixture containing varying amounts of the free acid; quaternary ammonium esters and unreacted anhydride can be used to prepare oligomeric products or mixtures thereof by reaction with an appropriate oxirane compound in the second step of the process of Reaction Scheme I.

It will be appreciated that the oxirane group of epichlorohydrin and epibromohydrin is capable of esterifying free acids, but cannot esterify anhydrides. Accordingly, the initial reaction in the second step will be between the oxirane group and those free carboxcyclic acids present in the intermediate reaction mixture liberated as a result of the first step. Since the intermediate reaction product formed by reaction of PMDA with less than two moles of the quaternary ammonium alcohol is a mixture of various types of linking groups, various reactions will occur producing a mixture of products having a variety of structures. Thus, for example, a mole of ester/acid of PMDA can be reacted with one or two moles of a linking compound, as for example, epichlorohydrin or some other oxirane (such as epibromohydrin, glycidal, and propylene oxide) which reacts with the free acid group of the ester/acid to form the adduct containing free hydroxyls in the cis and trans positions. These hydroxyls, in turn, can react with unreacted PMDA in the mixture adding an additional pyromellitate ring to the oligomer, which ring may have free carboxyl groups and anhydride groups. The anhydride groups can react with any of the free hydroxyl group in the mixture, and the carboxy group can react with any oxirane in the reaction mixture as aforesaid. This alone will cause a plurality of dimers, trimers, tetramers, etc. to be formed, with predominant species being dimers and trimers so long as the proportion of unreacted PMDA in the first reaction product is relatively small. Furthermore, since a small proportion of the oxirane compound normally reacts to produce free primary alcohol (with the carboxyl of the ring linked to the 2-carbon rather than to the 1-carbon), more than one linking structure between rings will be formed on the reaction with unreacted anhydride groups. It is believed that the linking structures will be $-C(O)OCH(CH_2X)CH_2OC(O)-$ in both instances, but that the structure will be reversed in direction when the pendant alcohol is primary. In all cases the free acids reacted with epichlorohydrin to produce pendant primary or secondary alcohols. The pendant alcohols then react with anhydrides on adjacent rings to produce the linking groups and free carboxyls, which then react with epichlorohydrins to produce "A" groups.

As indicated above, the mole ratio of quaternary ammonium alcohol to pyromellitic dianhydride in the first step of the present invention is critical to the formation of the monomeric and oligomeric products and mixtures thereof. When oligomeric products are desired, the mole ratio is between about 1:0.55 and about 1:1, and when monomeric products are desired the mole ratio is between about 1 and about 0.5. Preferably this ratio is between about 1:0.6 and about 1:0.85, for oligomeric materials, and is preferably between about 1 and about 0.5 for monomeric materials. In the more preferred embodiments, this ratio is between about 1:0.65 and about 1:0.75 for oligomeric materials, and between about 1 and about 0.5 for monomeric materials.

Alternatively, the oligomeric products in which the linking group is derived from oxirane compounds can also be prepared by reacting the monomeric compounds of the formula:

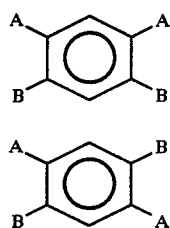

(I)

(II)

with pyromellitic dianhydride. In this modification, the primary or secondary alcohol moiety of the A group reacts with the anhydride moiety of the pyromellitic dianhydride. Reaction between the alcohol moiety and the anhydride producing an ester group linking one or more of the monomeric compounds and one or more moieties containing free acid groups thereby forming the oligomeric compounds. The free acid group can then be reacted with an oxirane compound to form the corresponding ester. This process is a modification of the process described in U.S. Pat. No. 4,414,277.

The oligomeric compounds of this invention containing linking groups which are not derived from oxirane compounds can be prepared by a modification of the procedure of Reaction Scheme II. In this modification, the diester/diacid chloride intermediates are reacted with a bifunctional compound of the formula:

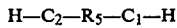

wherein $C_1$, $C_2$ and $R_5$ are as described above, preferably in the presence of an acid acceptor such as pyridine or triethylamine. In this reaction, the amino, mercapto and/or hydroxyl terminal groups of the bifunctional compound will react with acid chloride functions of the diester/diacid chloride intermediates forming a linking moiety of the formula $—C_2—R_5—C_1—$ which links the two or more diester/diacid chloride intermediate. The mole ratio of diester/diacid chloride intermediate to bifunctional compound is critical to the formation of oligomeric products. For example, if two moles of the bifunctional compound per mole of diester/diacid chloride intermediate is used, the product, on average will have two bifunctional compound substituted at the diacid chloride functions by way of an oxygen, a nitrogen or a sulfur atoms of the bifunctional compound. It will be appreciated, however, that this product represents only an average with the actual reaction mixture containing some unreacted diester/diacid chloride intermediates, some acid chloride intermediate substituted with one or two bifunctional compounds diester, etc. The use of from two moles to three moles of the diester/diacid chloride intermediate per two moles of bifunctional compound would be expected to result in a coupling reaction forming a reaction mixture containing compounds which two or more in which pyromellitate rings are linked by the residue of one or more bifunctional compounds. In this process, the initial reaction will be reaction between two moles of the bifunctional compound and one mole of a diester/diacid chloride intermediate to form the adduct consisting of a diester pyromellitate nucleus having free moieties of the formula:

One or both or these substituted at the acid chloride functions of these pendant groups can then react with a diacid chloride moiety of unreacted diester/diacid or one or two chloride intermediates in the reaction mixture adding one or two additional pyromellitate rings to the compound, which rings includes free acid/chloride groups. The free acid chloride groups can then react with any free hydroxyl, mercapto or amino group in the reaction mixture. This alone will cause a plurality of dimers, trimers, tetramers and the like to be formed.

This procedure can continue until the desired number of pyromellitate rings are linked in the oligomer. Then the reaction can be terminated by addition of a capping compound such as a compound of the formula

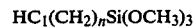

As indicated above, any of the preferred solvents useful in forming the compounds of Mares et al., Oxenrider et al. and Oxenrider may be used as the reaction solvent the processes of Reaction Schemes I and II. Illustrative of such solvents are dimethylformamide, N-methylpyrrolidone, and aliphatic esters having boiling points below about 150° C., such as ethyl acetate and butyl acetate. Other suitable solvents include aliphatic ketones such as methyl isobutyl ketone.

Reaction temperatures are not critical and can vary widely. It is preferred that the temperature during the first step of each reaction is between about 15° C. and about 80° C., more preferably between about 40° and about 50° C. It is preferred that the temperature during the subsequent steps be between about 45° C. and about 100° C., more preferably from about 50° C. to about 75° C. The reaction times are not critical and can vary widely. But it is preferred that the first step of both processes be run long enough to react essentially all (e.g. about 90% or greater) of the alcohol introduced; that the second step of both processes be long enough to react essentially all free carboxyls (e.g. until at least about 90%, or more, preferably at least about 95% or more, of the free carboxyls titratable by alcoholic KOH are consumed); and that the third step of the process of Reaction Scheme II be conducted long enough to react essentially all (e.g. until at least about 90%, or more, and preferably about 95% or more) of the acyl chloride functions.

Reaction pressures are also not critical and can be varied widely. Atmospheric pressure is preferred primarily for convenience.

Solvent amounts are not critical and can be varied widely. Usually, sufficient solvent is used to keep at least half of the pyromellitate and alcohol in solution (since precipitate can redissolve into solution as it reacts), and preferably in an amount sufficient to keep all of the reactants, intermediates and products in solution.

Once formed, the monomeric and/or oligomer-containing mixtures of the present invention are normally recovered from the solvent in a manner analogous to that employed in the above Mares et al., Oxenrider et al. and Oxenrider patents. Thus, for example, the entire reaction mixture may be added to a non-solvent such as water when N-methylpyrrolidone is used as solvent or a volatile ester or ketone solvent may be distilled from the reaction mixture. In either case, it is preferred to wash the initial product at least once with water in order to remove any remaining solvent and/or catalyst and/or unreacted reactants, and especially unreacted oxirane compounds.

The monomeric and oligomeric products may then be applied to a fiber, for example polyamide or polyester fibers, via an organic solvent such as acetone, methanol or dioxane. The compound may further be applied to the fiber as an emulsion along with other fiber treating agents, as for example the antisoiling additives described in U.S. Pat. No. 4,209,610 and especially as a component of spin finishes used to reduce friction of the fiber during processing. These products may be used alone or in combination with other surface treating materials, as for example, those described in U.S. Pat. No. 4,414,277.

Fibers for use with the compounds of this invention can vary widely. Suitable fibers include poly(caproamide) (nylon 6), poly(hexamethylene diamine adipate) (nylon 66) and other polyamides of both the poly(amino acid) type and poly(diamine dicarboxylate) types such as poly(hexamethylene diamine sebacate) known as nylon 6-12. Also suitable are polyesters such as poly(ethylene terephthalate) (PET), poly(butylene terephthalate) and the like. Levels of application are not critical and can vary widely. In general, levels on a surface modifier/fiber basis similar to the above patents are suitable (e.g. 0.075-0.25% surface modifier) for use in the practice of this invention.

Subsequent to fiber utilization, it is preferred that the treated fiber be annealed to improve the adherence of the treating agent to the fiber. Annealing conditions are generally between about 50° and about 160° C.; but with the present products, it is preferred that the annealing conditions be between about 65° and about 120° C.

The following specific examples are presented to more particularly illustrate the invention and are not to be construed as limitation of the scope of the invention.

EXAMPLE I

Preparation of 3-Hydroxypropyl Dimethyl Octadecyl Ammonium Bromide

A mixture of stearyl bromide (100 ml, 0.297 meq) and N,N-dimethylaminopropanol (35.2 ml, 0.297 meq) in dry acetonitrile (140 ml) was stirred under nitrogen at reflux (82° C.) for 16 hours. The mixture solidified on cooling and was recrystallized by adding acetone (1.0 l), heating to dissolve the solids, and storing the solution at room temperature for 1 hour then at 0° C. for 1 hour. The precipitate was collected on a frit, washed with acetone (200 ml), then dried at room temperature/0.1 mm Hg to give a white solid (104 g, 80% yield) m.p. 92°-94° C. Proton NMR confirmed the desired structure.

EXAMPLE II

Preparation of 3-Hydroxypropyl Dimethyl Butyl Ammonium Bromide

Employing the procedure of EXAMPLE I, 9.0 ml of butyl bromide and 10.0 ml. of N,N-dimethyl-aminopropanol was reacted in dry acetonitrile (50 ml) for 84 hrs at 80° C. to provide crude product which was recrystallized from ether to provide 19.1 g (94%) of the desired product. Proton NMR confirmed the desired structure.

EXAMPLE III

Preparation of 3-Hydroxypropyl Dimethyl Nonyl Ammonium Bromide

Employing the procedure of EXAMPLE II, 18.5 ml. of nonyl bromide was reacted with 11.5 ml. of N,N-dimethyl-aminopropanol in 50 ml. of acetonitrile to provide a crude product which was recrystallized from ether to give 28.9% g (96%) of a white solid. Proton NMR confirmed the desired structure.

EXAMPLE IV

Preparation of 3-Hydroxypropyl Dimethyl Dodecyl Ammonium Bromide

Employing the procedure of EXAMPLE II, 23.3 ml. of dodecyl bromide was reacted with 11.5 ml. of N,N-dimethylaminopropanol in 50 ml. of acetonitrile to provide a crude product which was recrystallized from ether to give 26.2 g of a white solid. Proton NMR confirmed the desired structure.

EXAMPLE V

Preparation of 3-Hydroxypropyl Dimethyl Tetradecyl Ammonium Bromide

Employing the procedure of EXAMPLE II, 53.6 ml. of tetradecyl bromide was reacted with 21.4 ml. of N,N-dimethylaminopropanol in 85 ml of acetonitrile to provide a crude product which was recrystallized from acetone to give 57.3 g (84%) of white solid. Proton NMR confirmed the desired structure.

EXAMPLE VI

Preparation of 3-Hydroxypropyl Dimethyl Hexadecyl Ammonium Bromide

Employing the procedure of EXAMPLE II, 15 ml. of hexadecyl bromide was reacted with 5.8 ml. of N,N-dimethylaminopropanol in 25 ml of acetonitrile to provide a crude product which was recrystallized from acetone to give 13.0 (65%) of a white solid. Proton NMR confirmed the desired structure.

EXAMPLE VII

Preparation of 3-Hydroxypropyl Dimethyl 2-(2-[2-methoxy]ethoxy)ethoxyethyl Ammonium Bromide Employing the procedure of EXAMPLE II, 66.0 g of 2-(2-[methoxy]ethoxy)ethoxyethyl bromide was reacted with 34.4 ml. of N,N-dimethylaminopropanol, in 175 ml of acetonitrile to provide an oily crude product which was shaken with ether and dried at 50°/1 mm Hg to give 87.5 g (91%) of material. Proton NMR confirmed the desired structure.

EXAMPLE VIII

Preparation of 3-Hydroxypropyl Dimethyl Methoxy-polyethoxyethyl Ammonium Bromide Employing the procedure of EXAMPLE II, 10.0 g of methoxypolyethyoxyethyl bromide was reacted with 2.9 ml. of N,N-dimethylaminopropanol, in 15 ml. of acetonitrile to provide 10.7 g (86%) of oily material. Proton NMR confirmed the desired structure.

EXAMPLE IX

Preparation of 3-Hydroxypropyl Dimethyl (Tripropylene glycol methyl ether) Ammonium Bromide Employing the procedure of EXAMPLE II, 5.0 g of bromotripropylene glycol methyl ether was reacted with 2.1 ml of N,N-dimethylaminopropanol in 10 ml. of 2-methoxyethanol to provide a crude product which was washed with water to give 4.4 g (66%) of oil. Proton NMR confirmed the desired structure.

EXAMPLE X

Preparation of 3-Hydroxypropyl Dimethyl Benzyl Ammonium Chloride

Employing the procedure of EXAMPLE II, 9.7 ml. of benzyl chloride was reacted with 10.0 ml. of N,N-dimethylaminopropanol in 50 ml of acetonitrile to provide a crude product which was recrystallized from ether to give 15.3 g (79%) of a white solid. Proton NMR confirmed the desired structure.

EXAMPLE XI

Preparation of 3-Hydroxypropyl Dimethyl Nonyl Ammonium Iodide

Employing the procedure of EXAMPLE II, 20.0 g of nonyl iodide was reacted with 14.3 ml of N,N-dimethylaminopropanol in 50 ml of acetonitrile to provide a crude product which was slurried with ether to give 27 g (77%) of an amber oil which solidified on standing. Proton NMR confirmed the desired structure.

EXAMPLE XII

Preparation of 3-Hydroxypropyl Dimethyl Octadecyl Ammonium Chloride

Employing the procedure of EXAMPLE II, 31.3 g of N,N-dimethyloctadecylamine was reacted with 9.0 g of 3-chloropropanol in 100 ml of acetonitrile to provide a crude product which was recrystallized from acetone to give 29.0 g (70%) of white solids. Proton NMR confirmed the desired structure.

EXAMPLE XIII

Preparation of 2-(2-[2-Hydroxy]ethoxy) Ethoxyethyl Triethyl Ammonium Chloride

A solution of 43.5 ml of 2-(2-[2-chloroethoxy]ethoxy)ethanol 83.3 ml of triethylamine, ml. of N,N-dimethylformamide, and 0.16 g of potassium iodide were stirred under nitrogen at 100° for 71 hours then cooled to room temperature, filtered, and evaporated at 65° C./0.15 mm Hg to give 71 g of light brown oil.

EXAMPLE XIV

Pyromellitic dianhydride (1.3 g, 12 meq) and 3-hydroxypropyl dimethyl octadecyl ammonium bromide (5.2 g, 12 meq) were stirred under nitrogen in dry, N,N-dimethylformamide (25 ml) with triethylamine catalyst (0.1 ml) at 50° C. for 18 hours. Epichlorohydrin (1.9 ml, 24 meq) was added and the mixture was stirred for 20 hours at 50° C. The product was recovered by evaporating the reaction mixture at 50° C./0.1 mm Hg to give an amber semi-solid (6.5 g). Carbon and proton NMR's of quaternary nitrogen-containing products were generally broadened and rendered useless as an analytical tool.

EXAMPLE XV

Employing the procedure of EXAMPLE XIV, 5.0 g of 3-hydroxypropyldimethylbutylammonium bromide was reacted with pyromellitic dianhydride followed by reaction with 3.3 ml. of epichlorohydrin to provide a brown semi-solid (14 g).

EXAMPLE XVI

Employing the procedure of EXAMPLE XIV, 5.0 g of 3-hydroxypropyldimethylnonylammonium bromide was reacted with pyromellitic dianhydride followed by reaction with 2.5 ml. of epichlorohydrin to provide 10.5 g of product.

EXAMPLE XVII

Employing the procedure of Example XIV, 5.0 g of 3-hydroxypropyl dimethyl dodecyl ammonium bromide was reacted with pyromellitic dianhydride followed by reaction with 2.2 ml. of epichlorohydrin to provide 9.7 g of product.

EXAMPLE XVIII

Employing the procedure of Example XIV, 4.0 g of 3-hydroxypropyldimethyl 2-(2-[2-methoxy]ethoxy)ethoxyethyl ammonium bromide was reacted with pyromellitic dianhydride (1.2 g, 12 meq) followed by reaction with 1.9 ml of epichlorohydrin to provide 9.5 g of product.

EXAMPLE XIX

Employing the procedure of Example XIV, 4.0 g of 3-hydroxypropyl dimethyl (tripropylene glycol methyl ether) ammonium bromide was reacted with pyromellitic dianhydride (1.3 g, 12 meq) followed by reaction with 1.7 ml. of epichlorohydrin to provide 6.7 g of product.

EXAMPLE XX

Employing the procedure of Example XIV 5.0 g of 3-hydroxypropyl dimethyl benzyl ammonium chloride was reacted with pyromellitic dianhydride (1.3 g. 12 meq) followed by reaction with 3.4 ml. of epichlorohydrin to provide 9.7 g of product.

EXAMPLE XXI

Employing the procedure of Example XIV, 5.0 g of 3-hydroxypropyl dimethyl octadecyl ammonium chloride was reacted with pyromellitic dianhydride (1.3 g, 12 meq) followed by reaction with 2.0 ml. of epichlorohydrin to provide 7.5 g of product.

EXAMPLE XXII

Employing the procedure of Example XIV, 4.0 g of 3-hydroxypropyl dimethyl nonyl ammonium iodide was reacted with pyromellitic dianhydride (1.3 g, 12 meq) followed by reaction with 1.7 ml. of epichlorohydrin to provide 7.5 g of product.

EXAMPLE XXIII

Pyromellitic dianhydride (1.0 g, 9.2 meq) and 3-hydroxypropyl dimethyl octadecyl ammonium bromide (4.0 g, 9.2 meq) were stirred under nitrogen in dry, N,N-dimethylformamide (20 ml) with triethylamine catalyst (0.05 ml) at 50° C. for 20 hours. Epichlorohydrin (2.0 ml, 26 meq) was added and the mixture was stirred at 50° C. for 4 hours. More pyromellitic dianhydride (0.5 g, 4.6 meq) was added and the mixture stirred at 50° C. for 18 hours. The product was recovered by evaporating the reaction mixture at 50°/0.1 mm Hg to give a thick red oil (7.6 g).

EXAMPLE XXIV

Employing the procedure of Example XXIII, 5.0 g of 3-hydroxypropyl dimethyl hexadecyl ammonium bromide was reacted with pyromellitic dianhydride followed by reaction with 2.6 ml. of epichlorohydrin to provide 11.6 g of product.

EXAMPLE XXV

Employing the procedure of Example XXIII, 3.1 g of 3-hydroxypropyldimethylmethoxypolymethoxyethyl ammonium bromide was reacted with pyromellitic dianhydride followed by reaction with 1.3 ml. of epichlorohydrin to provide 7.6 g of product.

EXAMPLE XXVI

Employing the procedure of Example XXIII, 5.0 g of 3-hydroxypropyldimethyloctadecylammonium chloride was reacted with pyromellitic dianhydride followed by reaction with 3.0 ml. of epichlorohydrin to provide 8.7 g of product.

EXAMPLE XXVII

Employing the procedure of Example XXIII, 5.0 g of 2-hydroxyethyldimethyloctadecylammonium bromide was reacted with pyromellitic dianhydride followed by reaction with 2.9 ml. of epichlorohydrin to provide 9.6 g of product.

EXAMPLE XXVIII

Pyromellitic dianhydride (1.2 g, 11 meq) and 3-hydroxypropyl dimethyl octadecyl ammonium bromide (5.0 g, 11 meq) were stirred under nitrogen in dry N,N-dimethylformamide (25 ml) at 50° C. for 18 hours. The product was recovered by evaporating the mixture at 50° C./0.5 mm Hg to give a white suspension which was slurried in ether (250 ml), collected on a frit, and washed with ether (25 ml). The solids were dried at room temperature 1/mm Hg to give a white powder (5.5 g).

EXAMPLE XXIX

The diester-diacid chloride is prepared by stirring the diquaternaryester-diacid (16.6 meg) described in Example XXVIII in dry ethyl acetate (45 ml) under nitrogen at 65° C. for 1 minute then cooling to 50° C. Oxalyl chloride (1.6 ml, 18 meq) in ethyl acetate (5 ml) is added. The mixture is stirred at 50° C. for 3 hours after which the mixture is cooled to room temperature. Triethylamine (2.4 ml) in ethyl acetate (5 ml) is added and the mixture stirred 1 hour. After cooling to room temperature, a mixture of glycidol (1.1 ml, 17 meq) triethylamine (2.3 ml) and ethyl acetate (10 ml) is added and the mixture is stirred at room temperature for 16 hours. The product is recovered by filtering away the solids and evaporating the filtrate at 40° C./0.1 mm.

EXAMPLE XXX

The diquaternary ester-diacid (5.0 g, 9.2 meq) described in Example XXVIII was stirred in dry ethyl acetate (40 ml) with N,N-dimethylformamide catalyst (0.05 ml) under a dry atmosphere at 50° C. Oxalyl chloride (0.80 ml, 9.2 meq) in ethyl acetate (5 ml) was added and the mixture was stirred at 50° C. for 30 minutes. Triethylamine (2.7 ml, 19 meq) in ethyl acetate (10 ml) was added followed by 3-mercaptopropyltrimethoxysilane (1.7 ml, 9.2 meq) in ethyl acetate (5 ml) and the mixture was stirred at 50° C. for 18 hours. The product was recovered by filtering off the solids and evaporating the filtrate at 50° C./0.5 mm Hg to give an orange semi-solid (4.4 g).

EXAMPLE XXXI

Employing the procedure of Example XXX, N-methylaminopropyltrimethoxysilane (0.69 ml: 3.7 meq.) was reacted with pyromellitic dianhydride to provide 1.6 g of product.

EXAMPLE XXXII

Employing the procedure of Example XXX, 5.0 g of the diester-diacid described in Example XXIX was reacted with oxalyl chloride (1.6 ml.; 18 meq.) followed by reaction with 3-mercapto-propyltrimethoxysilane (3.4 ml.; 18 meq.) to provide 7.7 g of product.

EXAMPLE XXXIII

Performance Evaluation For Anti-Static Properties—Nylon 6

Solutions were prepared from the products of various Examples in 100 mL acetone. Swatches of nylon 6 fibers were dipped in the solutions, hand pressed between aluminum foil and plate, air dried for 1–3 hours and then annealed for 30 minutes at a selected temperature (room temperature, 80° C. and 100° C.). Each sample swatch was then tested and rated for static properties (surface resistivity) initially, and after a selected number of laundry cycles by the procedures of AATC Test No. 76-1969. This test is designed for determining the surface electrical resistivity of fabrics; electrical resistivity influences the accumulation of electrostatic charge on a fabric. Soap was not used during laundering.

In practice, fabric strips one-inch wide are coated with a solution (0.25%) of the material to be tested, annealed at a given temperature, then painted with conductive paint leaving a one-inch gap at the center of the strip. The strips are conditioned at 20% relative humidity and 21° C. for 18–24 hours; subsequent handling and tests are all done under these conditions. A Beckman Instruments Model L-8 megohmmeter is used for the measurements. Each strip is placed across the megohmmeter electrodes and 100 volts potential is applied; the resistivity is read directly from the instrument's meter. The values are recorded as a letter code where $A = 10^{11}$ ohms, $B = 10^{12}$ ohms, $C = 10^{13}$ ohms, $D = 10^{14}$ ohms, $E = 10^{15}$ ohms and $F = 10^{16}$ ohms. A nylon control was $> 10^{16}$ ohms under these conditions.

The results of this test are set forth in the following Table I.

TABLE I

| Exp No | Composition | Resistivities at Various Annealing Temperature | | |
|---|---|---|---|---|
| | | R.T. | 80° | 100° |
| 1 | Example XV | D | E | E |
| 2 | Example XVI | D | E | E |
| 3 | Example XXII | D | D | E |
| 4 | Example XVII | D | E | F |
| 5 | Example XIV | C | E | D |
| 6 | Example XXII | D | F | E |
| 7 | Example XVIII | C | B | C |
| 8 | Example XIX | D | E | F |
| 9 | Example XX | D | D | E |
| 10 | Example XXX | E | E | E |
| 11 | Example XXXII | C | C | D |
| 12 | Example XXXI | D | C | D |
| 13 | Example XXIV | C | C | D |
| 14 | Example XXIII | B | B | D |
| 15 | Example XXVI | D | D | D |
| 16 | Example XXV | C | C | F |

EXAMPLE XXXIV

Performance Evaluation for Anti-Static and Anti-Soiling Properties—Nylon 6

Using the procedure of EXAMPLE XXXIII, solutions containing varying amounts of products of various of the foregoing examples, and fluorinated pyromellitic tetraester and an oligomeric derivative thereof known for use as antisoiling agents were prepared and evaluated for surface resistivities and for oil repellency by the procedures of AATC Test No. 118-1966, initially and after being subjected to a number of laundry cycles. The results are set forth in the following Table II all percents are by weight based on the total weight of surface modifiers in the solution. In the table resistivity values are recorded using the letter code of EXAMPLE XXXIII, anti-soiling values are recorded as a number code where 1=excellent, 2=acceptable and 3=unacceptable, "S.R" is an abbreviation for surface resistivity, "A.S" is an abbreviation for anti-soiling, "DSR" is an abbreviation for the fluorinated pyromellitic tetraester, "OLIG" is an abbreviation for the oligomeric derivative of DSR, "Ex1" is an abbreviation for the product of Example XXIII, "Ex2" is an abbreviation for the product of EXAMPLE XIV, and "Ex3" is an abbreviation for the product of EXAMPLE XXV.

TABLE II

| CYCLE | PROPERTY EVALUATED | 25% Ex 1/75% DSR | | | 25% Ex 1/75% OLIG. | | |
|---|---|---|---|---|---|---|---|
| | | RT | 80° C. | 110° C. | RT | 80° C. | 110° C. |
| 0 | A.S. | 1 | 1 | 1 | 1 | 1 | 1 |
| | S.R. | E | D | D | F | E | E |
| 1 | A.S. | 1 | 1 | 1 | 1 | 1 | 1 |
| | S.R. | F | F | D | F | E | F |
| 2 | A.S. | 1 | 1 | 1 | 1 | 1 | 1 |
| | S.R. | D | F | F | F | F | F |
| 3 | A.S | — | — | 1 | 1 | 1 | 1 |
| | S.R. | — | — | F | D | E | F |
| 4 | A.S. | — | — | 1 | — | 1 | 1 |
| | S.R. | — | — | E | — | F | F |
| 5 | A.S. | — | — | 1 | — | 1 | 1 |
| | S.R. | — | — | E | — | — | — |
| 6 | A.S. | — | — | 1 | — | — | — |
| | S.R. | — | — | E | — | — | — |
| 7 | A.S. | — | — | 1 | — | — | — |
| | S.R. | — | — | F | — | — | — |

| CYCLE | PROPERTY EVALUATED | 35% Ex 1/65% DSR | | | 35% Ex 1/65% OLIG. | | |
|---|---|---|---|---|---|---|---|
| | | RT | 80° C. | 110° C. | RT | 80° C. | 110° C. |
| 0 | A.S. | 1 | 1 | 1 | 1 | 1 | 1 |
| | S.R. | D | D | F | E | F | F |
| 1 | A.S. | 1 | 1 | 1 | 1 | 1 | 1 |
| | A.S | F | E | F | E | D | E |
| 2 | A.S | 1 | 1 | 1 | 1 | 1 | 1 |
| | S.R. | F | E | F | F | F | E |
| 3 | A.S | — | — | 1 | 1 | 1 | 1 |
| | S.R. | — | — | F | F | E | F |
| 4 | A.S. | — | — | 1 | — | 1 | 1 |
| | S.R. | — | — | F | — | E | F |
| 5 | A.S. | — | — | 1 | — | 1 | 1 |
| | S.R. | — | — | E | — | E | F |
| 6 | A.S. | — | — | 1 | — | 1 | 1 |
| | S.R. | — | — | F | — | E | F |
| 7 | A.S. | — | — | — | — | — | 1 |
| | S.R. | — | — | F | — | — | F |

| CYCLE | PROPERTY EVALUATED | 50% Ex 1/50% DSR | | | 50% Ex 1/50% OLIG. | | |
|---|---|---|---|---|---|---|---|
| | | RT | 80° C. | 110° C. | RT | 80° C. | 110° C. |
| 0 | A.S. | 1 | 1 | 1 | 1 | 1 | 1 |
| | S.R. | D | E | F | F | E | D |
| 1 | A.S. | 1 | 1 | 1 | 1 | 1 | 1 |
| | A.S | F | F | F | F | F | E |
| 2 | A.S | 1 | 1 | 1 | 1 | 1 | 1 |
| | S.R. | F | C | E | F | F | F |
| 3 | A.S | — | 1 | 1 | — | 1 | 1 |
| | S.R. | — | F | F | — | F | F |
| 4 | A.S. | — | — | 1 | — | — | 1 |
| | S.R. | — | — | F | — | — | F |
| 5 | A.S. | — | — | 1 | — | — | 1 |
| | S.R. | — | — | F | — | — | F |
| 6 | A.S. | — | — | 1 | — | — | 1 |
| | S.R. | — | — | F | — | — | F |
| 7 | A.S. | — | — | 1 | — | — | — |
| | S.R. | — | — | F | — | — | — |

| CYCLE | PROPERTY EVALUATED | 25% Ex 2/75% DSR | | | 25% Ex 2/75% OLIG. | | |
|---|---|---|---|---|---|---|---|
| | | RT | 80° C. | 110° C. | RT | 80° C. | 110° C. |
| 0 | A.S. | 1 | 1 | 1 | 1 | 1 | 1 |
| | S.R. | E | F | F | F | F | F |
| 1 | A.S. | 1 | 1 | 1 | 1 | 1 | 1 |
| | S.R. | D | D | F | E | F | E |
| 2 | A.S. | 1 | 1 | 1 | 1 | 1 | 1 |
| | S.R. | F | C | F | D | E | D |
| 3 | A.S. | — | — | 1 | 1 | 1 | 1 |
| | S.R. | — | — | F | F | E | F |
| 4 | A.S. | — | — | 1 | 1 | 1 | 1 |
| | S.R. | — | — | F | F | F | E |
| 5 | A.S. | — | — | 1 | 1 | 1 | 1 |
| | S.R. | — | — | E | E | F | F |
| 6 | A.S. | — | — | 1 | 1 | 1 | 1 |
| | S.R. | — | — | F | F | E | E |
| 7 | A.S. | — | — | 1 | 1 | 1 | 1 |
| | S.R. | — | — | F | F | E | E |

| CYCLE | PROPERTY EVALUATED | 35% Ex 2/65% DSR | | | 35% Ex 2/65% OLIG.[2] | | |
|---|---|---|---|---|---|---|---|
| | | RT | 80° C. | 110° C. | RT | 80° C. | 110° C. |
| 0 | A.S. | 1 | 1 | 1 | 1 | 1 | 1 |
| | S.R. | E | D | F | F | — | F |
| 1 | A.S. | 1 | 1 | 1 | 1 | 1 | 1 |
| | S.R. | E | F | F | F | F | F |
| 2 | A.S. | 1 | 1 | 1 | 1 | 1 | 1 |
| | S.R. | E | F | F | F | F | E |
| 3 | A.S | — | 1 | 1 | 1 | 1 | 1 |
| | S.R. | — | F | D | E | F | E |
| 4 | A.S. | — | — | 1 | 1 | 1 | 1 |
| | S.R. | — | — | F | F | F | F |
| 5 | A.S. | — | — | 1 | 1 | 1 | 1 |
| | S.R. | — | — | F | F | E | F |
| 6 | A.S. | — | — | 1 | 1 | 1 | 1 |
| | S.R. | — | — | E | F | F | F |
| 7 | A.S. | — | — | — | 1 | 1 | 1 |
| | S.R. | — | — | — | F | E | F |

TABLE II-continued

| CYCLE | PROPERTY EVALUATED | 50% Ex 2/50% DSR RT | 80° C. | 110° C. | 50% Ex 2/50% OLIG. RT | 80° C. | 110° C. |
|---|---|---|---|---|---|---|---|
| 0 | A.S. | 1 | 1 | 1 | 1 | 1 | 1 |
|   | S.R. | — | — | E | — | — | — |
| 1 | A.S. | 1 | 1 | 1 | 1 | 1 | 1 |
|   | A.S | E | F | E | E | E | E |
| 2 | A.S | 1 | 1 | 1 | 1 | 1 | 1 |
|   | S.R. | E | D | D | C | F | C |
| 3 | A.S | — | 1 | 1 | 1 | 1 | 1 |
|   | S.R. | — | F | F | D | F | F |
| 4 | A.S. | — | — | 1 | — | — | 1 |
|   | S.R. | — | — | F | — | — | F |
| 5 | A.S. | — | — | 1 | — | — | 1 |
|   | S.R. | — | — | F | — | — | F |
| 6 | A.S. | — | — | 1 | — | — | 1 |
|   | S.R. | — | — | F | — | — | E |
| 7 | A.S. | — | — | — | — | — | — |
|   | S.R. | — | — | — | — | — | — |

| CYCLE | PROPERTY EVALUATED | 25% Ex 3/75% DSR RT | 80° C. | 110° C. | 25% Ex 3/75% OLIG. RT | 80° C. | 110° C. |
|---|---|---|---|---|---|---|---|
| 0 | A.S. | 1 | 1 | 1 | 1 | 1 | 1 |
|   | S.R. | F | D | F | F | F | D |
| 1 | A.S. | 1 | 1 | 1 | 1 | 1 | 1 |
|   | S.R. | D | E | E | D | E | F |
| 2 | A.S. | 1 | 1 | 1 | 1 | 1 | 1 |
|   | S.R. | F | F | D | D | F | F |
| 3 | A.S. | — | — | 1 | 1 | 1 | 1 |
|   | S.R. | — | — | F | D | E | F |
| 4 | A.S. | — | — | 1 | — | 1 | 1 |
|   | S.R. | — | — | F | — | F | F |
| 5 | A.S. | — | — | 1 | — | 1 | 1 |
|   | S.R. | — | — | E | — | E | E |
| 6 | A.S. | — | — | 1 | — | 1 | 1 |
|   | S.R. | — | — | E | — | F | F |
| 7 | A.S. | — | — | 1 | — | 1 | 1 |
|   | S.R. | — | — | F | — | F | E |

| CYCLE | PROPERTY EVALUATED | 35% Ex 3/65% DSR RT | 80° C. | 110° C. | 35% Ex 3/65% OLIG. RT | 80° C. | 110° C. |
|---|---|---|---|---|---|---|---|
| 0 | A.S. | 1 | 1 | 1 | 1 | 1 | 1 |
|   | S.R. | D | D | E | F | E | F |
| 1 | A.S. | 1 | 1 | 1 | 1 | 1 | 1 |
| 2 | A.S | F | F | D | E | E | F |
|   | A.S | 1 | 1 | 1 | 1 | 1 | 1 |
|   | S.R. | F | D | D | D | D | F |
| 3 | A.S. | — | 1 | 1 | 1 | 1 | 1 |
|   | S.R. | — | F | F | F | F | D |
| 4 | A.S. | — | — | 1 | — | 1 | 1 |
|   | S.R. | — | — | F | — | F | F |
| 5 | A.S. | — | — | 1 | — | 1 | 1 |
|   | S.R. | — | — | F | — | E | F |
| 6 | A.S. | — | — | 1 | — | 1 | 1 |
|   | S.R. | — | — | F | — | F | E |
| 7 | A.S. | — | — | — | — | — | 1 |
|   | S.R. | — | — | — | — | — | F |

| CYCLE | PROPERTY EVALUATED | 50% 3/50% DSR RT | 80° C. | 110° C. | 50% Ex 3/50% OLIG. RT | 80° C. | 110° C. |
|---|---|---|---|---|---|---|---|
| 0 | A.S. | 1 | 1 | 1 | 1 | 1 | 1 |
|   | S.R. | E | F | F | D | D | F |
| 1 | A.S. | 1 | 1 | 1 | 1 | 1 | 1 |
|   | S.R. | E | F | F | E | F | E |
| 2 | A.S. | 1 | 1 | 1 | 1 | 1 | 1 |
|   | S.R. | F | F | E | E | E | D |
| 3 | A.S. | — | — | 1 | — | 1 | 1 |
|   | S.R. | — | — | E | — | F | F |
| 4 | A.S. | — | — | 1 | — | 1 | 1 |
|   | S.R. | — | — | E | — | F | F |
| 5 | A.S. | — | — | 1 | — | 1 | 1 |
|   | S.R. | — | — | E | — | E | F |
| 6 | A.S. | — | — | 1 | — | 1 | 1 |
|   | S.R. | — | — | F | — | E | E |
| 7 | A.S. | — | — | — | — | — | 1 |
|   | S.R. | — | — | — | — | — | E |

EXAMPLE XXXVI

Performing Evaluation—Anti-Microbial Activity

A series of experiments were carried out to assess the anti-microbial activity of the compounds of this invention using the procedure of AATCC Test No. 100.

The results of the experiments are set forth in the following Table III.

TABLE III

BACTERIAL REDUCTION ASSAYS
PERCENT REDUCTION (5 HOUR)

| EXP. NO. | SAMPLE I.D. | S. AUREUS | K. PHEUMONIAE | TREATMENT |
|---|---|---|---|---|
| 1 | CONTROL FABRIC (no treatent) | 0 | 0 | Unannealed |
| 2 | DSR | 0 | 0 | Unannealed |
| 3 | OLIG | 0 | 0 | Unannealed |
| 4 | Ex 1 | 100 | 100 | Unannealed |
| 5 | Ex 3 | 0 | 0 | Unannealed |
| 6 | 35% Ex 1/65% DSR | 99.82 | 100 | Unannealed |
| 7 | 35% Ex 1/65% OLIG | 100 | 100 | Unannealed |
| 8 | 65% Ex 3/65% DSR | 0 | 0 | Unannealed |
| 9 | 35% Ex 3/65% OLIG | 0 | 0 | Unannealed |
| 10 | 35% Ex 1/65% DSR | 100 | 99.44 | Annealed 15 Min. @ 80° C. |
| 11 | Ex 1 | 100 | 100 | Annealed 15 Min. @ 80° C. |
| 12 | 35% Ex 1/65% DSR | 100 | 98.60 | Annealed 15 Min. @ 80° C. |
| 13 | 35% Ex 1/65% DSR | 100 | 100 | Annealed 15 Min. @ 80° C. |
| 14 | 35% Ex 3/65% DSR | 0 | 0 | Annealed 15 Min. @ 80° C. |
| 15 | 35% Ex 3/65% DSR | 0 | 0 | Annealed 15 Min. @ 80° C. |
| 16 | 35% Ex 3/65% DSR | 0 | 0 | Annealed 15 Min. @ 80° C. |
| 17 | 35% Ex 3/65% DSR | 0 | 0 | Annealed 15 Min. @ 80° C. |

What is claimed is:

1. A compound of the formula:

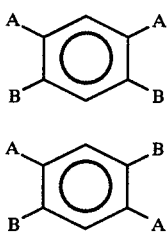 (I)

 (II)

or oligomers thereof wherein two or more of compounds I and II are limited at the "B" substituent site by divalent moieties of the formula:

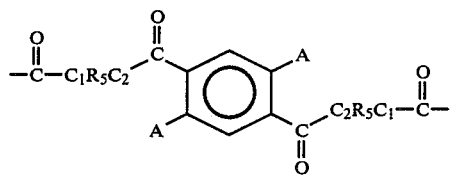

or

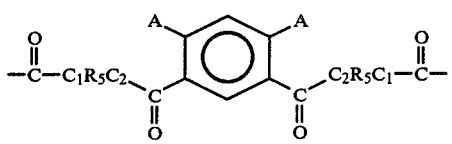

or

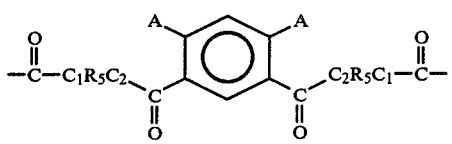

wherein:
B is a moiety of the formula

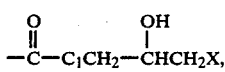

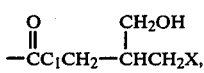

or

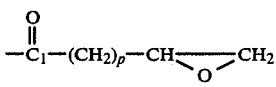

A is a moiety of the formula:

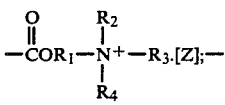

X is hydrogen, chloro or bromo;
Z is chloride, bromide or iodide;
$R_1$ is alkylene group having from about 1 to about 4 carbon atoms;
$R_2$ and $R_3$ are the same or different and are alkyl having from 1 to about 3 carbon atoms;
$R_4$ is alkyl having from 1 to about 20 carbon atoms, $(CH_2CH_2O)_nCH_3$, or $(CH_2CHCH_3O)_mOCH_3$;
n is an integer from 1 to about 10;
m is an integer from 1 to about 10;
p is 0 to about 4;
$C_1$ and $C_2$ are the same or different and are divalent oxygen, sulfur, amino or alkylamino moieties; and
$R_5$ is substituted or unsubstituted alkylene or arylene wherein permissible substituents are one or more halo or hydroxy groups.

2. A compound according to claim 1 wherein B is a moiety of the formula

or

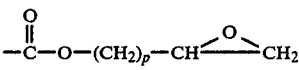

wherein
X is hydrogen, chloro or bromo;
p is 0 to about 4;
m is 1 to about 10;
$C_1$ is oxygen, sulfur, amino or alkylamino.

3. A compound according to claim 1 wherein A is a moiety of the formula:

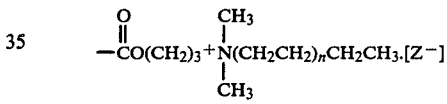

wherein n is 1 to about 8, and $Z^-$ is chloride, bromide or iodide; or

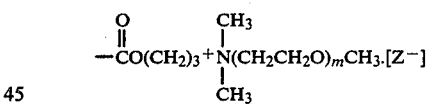

wherein m is from 2 to about 10, and Z is chloride, bromide or iodide; or

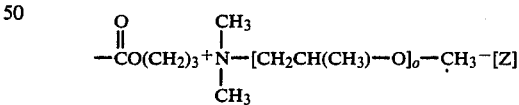

wherein 0 is from 1 to about 6, and $Z^-$ is chloride, bromide or iodide.

4. A compound according to claim 2 wherein B is a moiety of the formula:

wherein x is a hydrogen, chloro or bromo.

5. A compound according to claim 4 wherein X is chloro.

6. A compound according to claim 3 wherein A is a moiety of the formula:

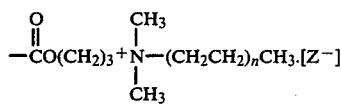

wherein n is from about 2 to about 8 and Z⁻ is chloride or bromide.

7. A compound according to claim 6 wherein Z⁻ is chloride.

8. A compound of the formula:

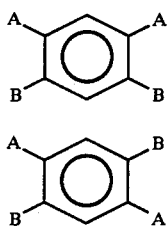

(I)

(II)

or oligomers thereof wherein two or more of components I and II are linked at the "B" substituents site by divalent moieties of the formula

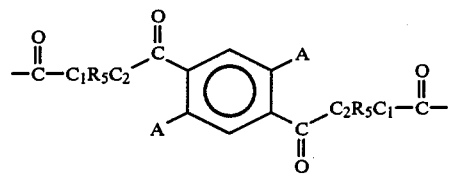

or

or

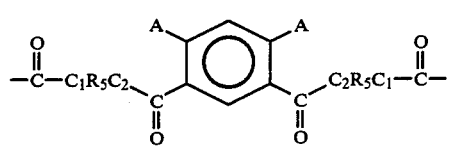

wherein:
B is a moiety of the formula:

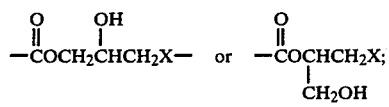

A is a moiety of the formula:

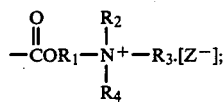

X is hydrogen, chloro or bromo;
Z is chloride, bromide or iodide;
$R_1$ is alkylene group having from about 1 to about 4 carbon atoms;
$R_2$ and $R_3$ are the same or different and are alkyl having from 1 to about 3 carbon atoms;
$R_4$ is alkyl having from 1 to about 20 carbon atoms, $(-H_2CH_2O)_nCH_3$, or $(CH_2CHCH_3O)_mCH_3$;

n is an integer from 1 to about 10;
m is an integer from 1 to about 10;
$C_1$ and $C_2$ are divalent oxygen; and
$R_5$ is substituted or unsubstituted alkylene or phenylene, wherein permissible substituents are one or more halo or hydroxy groups.

9. A compound according to claim 8 wherein:
$R_4$ is alkyl having from 1 to about 20 carbon atoms.

10. A compound according to claim 8 wherein:
$R_5$ is substituted or unsubstituted alkylene wherein permissible substituents are one or more halo or hydroxy groups.

11. A non-oligomeric compound according to claim 1.

12. An oligomeric compound according to claim 1.

13. A compound of the formula:

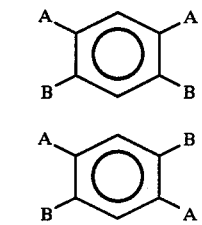

(I)

(II)

wherein:
B is a moiety of the formula:

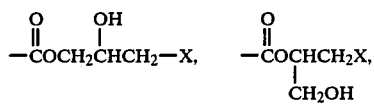

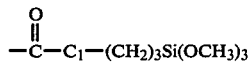

or

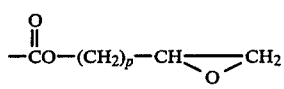

A is a moiety of the formula:

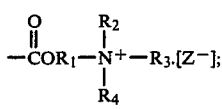

X is hydrogen, chloro or bromo;
Z is chloride, bromide or iodide;
p is an integer from 0 to about 4;
$R_1$ is alkylene group having from about 1 to about 4 carbon atoms;
$R_2$ and $R_3$ are the same or different and are alkyl having from 1 to about 3 carbon atoms;
$R_4$ is alkyl having from 1 to about 20 carbon atoms, $(CH_2CH_2O)_nCH_3$, or $(CH_2CHCH_3O)_mCH_3$;
n is an integer from 1 to about 10;
m is an integer from 1 to about 10; and
$C_1$ is divalent oxygen, sulfur, amino or alkylamine moieties; and
$R_5$ is substituted or unsubstituted alkylene or phenylene wherein permissible substituents are one or more fluoro, chloro, bromo, or hydroxy groups.

14. A compound according to claim 13 wherein $C_1$ is divalent oxygen.

15. A compound according to claim 14 wherein $R_5$ is alkylene.

* * * * *